United States Patent [19]

Hu et al.

[11] Patent Number: 4,786,556

[45] Date of Patent: Nov. 22, 1988

[54] POLYMERIC ARTICLES HAVING ENHANCED ANTITHROMBOGENIC ACTIVITY

[75] Inventors: Can B. Hu, Dayton; Donald D. Solomon, Spring Valley, both of Ohio

[73] Assignee: Becton, Dickinson and Company, Franklin Lakes, N.J.

[21] Appl. No.: 77,468

[22] Filed: Jul. 24, 1987

Related U.S. Application Data

[62] Division of Ser. No. 843,323, Mar. 24, 1986, Pat. No. 4,720,512.

[51] Int. Cl.$^4$ .................. B32B 27/08; B32B 27/36
[52] U.S. Cl. .................................. 428/412; 428/421; 428/422; 428/423.5; 428/423.7; 428/424.8; 428/425.5; 428/447; 428/473.5; 428/474.4; 514/822; 523/112

[58] Field of Search ................ 428/423.5, 423.7, 422, 428/447, 412, 421, 424.8, 474.4, 425.5, 473.5; 427/2; 525/54.2, 54.1; 524/233; 523/112; 514/822

[56] References Cited

U.S. PATENT DOCUMENTS

| | | | |
|---|---|---|---|
| 3,457,098 | 7/1969 | Leininger et al. | 427/2 X |
| 3,617,344 | 11/1971 | Leininger et al. | 428/422 |
| 3,844,989 | 10/1974 | Harumiya et al. | 525/54.2 X |
| 3,846,353 | 11/1974 | Grotta | 525/54.2 X |
| 3,853,804 | 12/1974 | Yen et al. | 524/233 |
| 4,521,564 | 6/1985 | Solomon et al. | 525/54.1 |

Primary Examiner—Thomas J. Herbert
Attorney, Agent, or Firm—Richard E. Brown

[57] ABSTRACT

Plastic articles having enhanced antithrombogenic activity due to the presence or hydrophobic materials attached to amine compounds bonded on the surface of the plastic which repel bonded antithrombogenic agents outwardly from the plastic surface, making them more readily available to the blood for subsequent thrombus inhibition.

13 Claims, 3 Drawing Sheets

POLYMERIC ARTICLES HAVING ENHANCED ANTITHROMBOGENIC ACTIVITY

This is a division of application Ser. No. 843,323, filed 3/24/86, now U.S. Pat. No. 4,720,512.

BACKGROUND

This invention relates to an antithrombogenic-containing polymeric material and process for making the same. More particularly, the invention relates to a method for preparing antithrombogenic polymeric articles which employ covalently bonded hydrophobic groups bonded to the polymeric surface to provide increased antithrombgenic activity.

Extensive investigations have been undertaken over many years to find materials that will be biologically and chemically stable towards body fluids. This area of research has become increasingly important with the development of various objects and articles which can be in contact with blood, such as artificial organs, vascular grafts, probes, cannulas, catheters, hyperalimentation catheters and other long indwelling vascular catheters and the like.

Artificial materials are being increasingly used as blood contact devices and may be subject to potential generation of thrombus. When blood contacts foreign materials a complex series of events occur. These involve protein deposition, cellular adhesion and aggregation, and activation of blood coagulation schemes. Considerable research effort has been focused on this blood-material-interaction in the last twenty years with such devices. The overall objective of these investigations has been to minimize the potential for thrombus formation, such as the device when introduced into the body upon contact with blood.

Various methods have been devised for producing such a material, most of which involve chemically bonding a quaternary ammonium salt to the polymer and then heparinizing the same. Usually, this is done by incorporating an amine in the polymer, quaternizing the amine, and then heparinizing or bonding an antibiotic to the quarernized material.

In one method taught by R. I. Leininger and G. A. Grode, U.S. Pat. No. 3,457,098, a quaternary amine is incorporated into an epoxy resin. Subsequent exposure to sodium heparinate dissolved in water then results in ionically bound heparin. The polymer systems are essentially epoxy resins which are rigid polymers which are not suitable for forming medical devices such as catheters or other devices requiring extrusion. These polymers also are not appropriate where flexibility in the device is required.

R. I. Leininger and R. D. Falb disclose in U.S. Pat. No. 3,617,344 another process for binding heparin. This system differs from the previous system in that low molecular weight chloromethyl groups are absorbed to the surface of a polymer substrate. Subsequent amination by a tertiary amine and quaternization resulted in a positively charged surface for binding with heparin. The concept, in general, embodies the use of low molecular weight quaternized groups to ionically bind heparin.

U.S. Pat. No. 3,846,353 to H. M. Grotta involves use of long chain alkyl quaternary amines on the surface of a polymer wherein the positively charged surface is exposed to a solution of sodium heparinate. The amines are dissolved in an organic solvent consisting of toluene, petroleum ether and mixtures thereof. One primary deficiency of the Grotta method is the use of toluene as a coating solvent. Toluene, when used with latex materials, results in a swelling of the products and destruction of essential elastic properties, rendering itself practically useless. In particular, this effect is seen with balloons present on balloon catheters wherein the balloon component becomes extremely fragile and is basically destroyed. Residues of toluene that may remain on the devices from processing which are targeted for internal use are thus harmful to the ultimate user. A second deficiency of ionically bonded systems is the short lifetime of the ionically bonded heparin due to desorption.

S. Yen and A. Rembaum prepared a neutral polyurethane elastomer which is subsequently quaternized and ionically bonded to heparin, U.S. Pat. No. 3,853,804. The main disadvantage of this system is that it is a chemical complex and toxic solvents are used to achieve solubility when coating. The coating technique, however, is difficult to perform due to the solvent (DMF) requirement. The patent of N. Harumiya et al., U.S. Pat. No. 3,844,989, describes a polymer composition of water-insoluble cationic copolymers having hydrophilic components, quaternary amine groups, and hydrophobic moieties. Heparin is bonded ionically to the quaternary ammonium groups via absorption after the polymer components are contacted with a heparin solution. This method involves use of complex synthesis procedures and is not readily applicable to coating other polymeric or non-polymeric materials.

U.S. Pat. No. 4,521,564 to Solomon et al. discloses antithrombogenic polyurethane polymers having the antithrombogenic material covalently bound to the polyurethane. The polyurethane polymer material is treated with a solution of a polymeric amine selected from the group consisting of a polyvinyl amine. a polyalkylenimine having 2 to 4 carbon atoms per amine unit and mixtures thereof so that the polymeric amine becomes covalently bonded to the polyurethane substrate. An antithrombogenic agent is then covalently bonded to the polymeric amine.

It would be desirable to provide a material which has excellent biological and chemical stability towards body fluids, namely blood, and which retains its antithrombogenic agent and antibiotic effect for a long term while being slowly leachable when in contact with blood. It would also be desirable to provide materials which have enhanced antithrombogenic activity.

The present invention accomplishes all of these needs and improves on the prior art compositions and methods of enhancing the availability of the antithrombogenic agent to blood, thereby increasing the agent's activity. Consequently, enhanced hemocompatibility of the products of this invention is also achieved. More particularly, the present invention concerns articles having antithrombogenic properties comprising:

(a) a polymeric solid support structure (b) a polymeric material rich in amine content which serves as a substrate for an antithrombogenic agent, said polymeric material being selected from the group consisting of primary amines having a carbon chain length of from 2 to 10,000, a polyalkylenimine having 2 to 4 carbon atoms per amine unit and mixtures thereof bonded to said polymeric support structure; and (c) an antithrombogenic agent covalently bonded to said polymeric material rich in amine content: wherein the activity of the antithrombogenic agent is enhanced by the hydrophobic material or functional groups covalently bonded to the substrate surface.

Those polymeric materials rich in amine content which serve as a substrate. e.g., bonding site, for the antithrombogenic agent, are preferably amine rich polyurethane urea polymers (referred to herein as APU polymers). These polymers are prepared as solutions which are then used to coat the polymeric support structure. For example. if the support structure is a cathether, tubing or other device, it can be dipped, brushed, sprayed or otherwise coated with the amine rich material. The coating bonds to the support structure surface, providing a site on which antithrombogenic materials can subsequently be attached covalently. However, unlike the prior art, the instant invention further prepares the amine rich substrate surface prior to bonding the antithrombogenic agent to the amine substrate. This further treatment comprises the introduction of hydrophobic materials or groups onto the substrate surface.

Preferred polymeric material rich in amine content include polyether based urethaneureas such an poly(ethylene oxide) urethane-urea, poly(propylene oxide) urethaneurea, poly(tetramethylene oxide) urethaneurea; polyester based urethaneureas such as poly(ethylene adipate) urethaneurea, poly(propylene adipate) urethaneurea, poly(tetramethylene adipate) urethaneurea, poly(hexamethylene adipate) urethane urea; other types of polyurethane ureas such as polycaprolactone urethaneurea and polybutadiene urethaneurea. Mixtures of these are also useful.

While the present invention has been described in terms of using the preferred amine rich polyurethane urea polymers as the substrate on which to attach the anlithrombogenio agent, it should be recognized that other substrate materials having active amine groups or groups such as polyamides, polyimides, polyalkylenimines, and polyvinyl amines may be used.

The enhanced antithrombogenic activity of the articles is believed to be due to the greater hydrophobic character imparted to the substrate surface. This effect is achieved by covalently bonding to the substrate surface a moiety selected from the group consisting of a flourine compound, a siloxane compound, a silazane compound, a silane compound, and mixtures thereof. In the case of the fluorine-containing compouds, the fluorine group is believed to covalently bond to the substrate surface. In the case of the siloxane, silane and silazane compounds, the silicone group is believed to covalently bond to the substrate surface.

Useful flourine-containing compounds include Freon ® compounds such as dichlorodifluoromethane, chlorotrifluoromethane, bromotrifluoromethane, tetrafluoromethane, chlorodifluoromethane, fluoroform, 1,1,2-trichlorotrifluoroethane, 1,2-dichlorotetrafluoroerhane, hexafluoroethane, tetrafluoroethylene, as well as hexafluoropropylene, boron trifluoride, silicon tetrafluoride., sulfur hexafluoride, sulfur tetrafluoride, tungsten hexafluoride, and fluorine among others. The preferred fluorinated compound is, however, hexafluoropropylene. Mixtures of these compounds are contemplated.

Those siloxane compounds useful have the formula:

wherein $R_1$, $R_2$ and $R_3$ are aliphatic or substituted aliphatic groups having an aliphatic carbon chain of 1-4 carbons; and n is an integer from 1 to 100, preferably from 3 to 20. Thus, aliphatic chains of up to 4 carbons having a benzene ring or other aromatic or aliphatic group substitution thereon are contemplated.

Those silazanes useful include compounds corresponding to the formula:

wherein $R_1$, $R_2$, $R_3$ and $R_4$ can be alkyl $C_{1-4}$ or hydrogen.

Those silane compounds useful have the formula:

wherein, $R_1$, $R_2$, $R_3$ and $R_4$ are selected from the group consisting of aliphatic groups, substituted aliphatic groups, aromatic groups, substituted aromatic groups, halogens, alkoxyl groups, vinyl groups and mixtures thereof.

The bonding of the fluorine, siloxane, silane and/or silazane moieties to the polymeric substrate surface is accomplished via glow discharge (ionized gas) treatment. This process is generally referred to in the art as plasma treatment. Plasma treatment is accomplished using a glow discharge ionization chamber, whereby samples are placed in the chamber and the chamber pressure is reduced to a minimal level. e.g., 0.1 torr or less, via a vacuum pump. The fluorine, siloxane, silane and/or silazane compounds are introduced in gaseous form into the plasma chamber to a desired level, e.g., about 0.3 torr, and purged to a level of about 0.1 torr to minimize potential contamination from other gases such as air. Purging is then repeated, and the final desired pressure of the gas is reached. For example, a pressure of about 0.1 to about 5 torrs is desired, and most preferably about 0.3 torrs. Radio frequency power is then generated and applied to the gas in the chamber for a fixed period of time. For example. about 10 to about 100 watts might be applied for a period of about 10 to about 20 minutes. The ionization reaction is allowed to proceed during this interval, at which time the power and vacuum are terminated and air or nitrogen gas is introduced to open the chamber.

It is necessary to maintain a balance of four factors during the plasma treatment of the substrate surface: power (wattage); exposure time (reaction time); gas flow rate; and chamber pressure. If too much wattage is applied for too long a period of time, the polymeric amine compound which serves as the site for bonding the antithrombogenic agent, could lose its functionality through cleavage or substitution by the gaseous moieties in the ionization chamber. Too little wattage and- /or exposure produce insufficient bonding of the hydrophobic moieties to the substrate surface. Thus, the wattage (power applied), exposure time of the substrate surface to the gaseous chamber, flow rate of the gas, as well as the chamber pressure, must be controlled within specified ranges. Variation of one of these factors may cause adjustment of the other factors in order to produce the desired result. The wattage applied should be from about 1 to 700 watts, preferably less than about 200 watts and most preferably from about 5 to about 50 watts. The flow rate of the gas in the chamber should be about 1 to about 500 standard cubic centimeters per minute (cc/min), preferably about 1 to about 100 cc/min, and most preferably about 1 to about 50 cc/min. The chamber pressure, during the treatment of the substrate surface, should be maintained in the range of about 0.1 to about 100 torrs (mm of mercury), preferably about 0.2 to about 10 torrs and most preferably about 0.3 to about 5 torrs. Exposure time of the substrate surface to the chamber atmosphere under the above ranges vary widely from a few minutes or hours to about 24 hours. Preferably, at 50 watts, 0.3 torrs and 5 cc/min, a time of about 10 minutes to 1 hour is sufficient to impart excellent hydrophobic character to the substrate surface.

Figure 1:
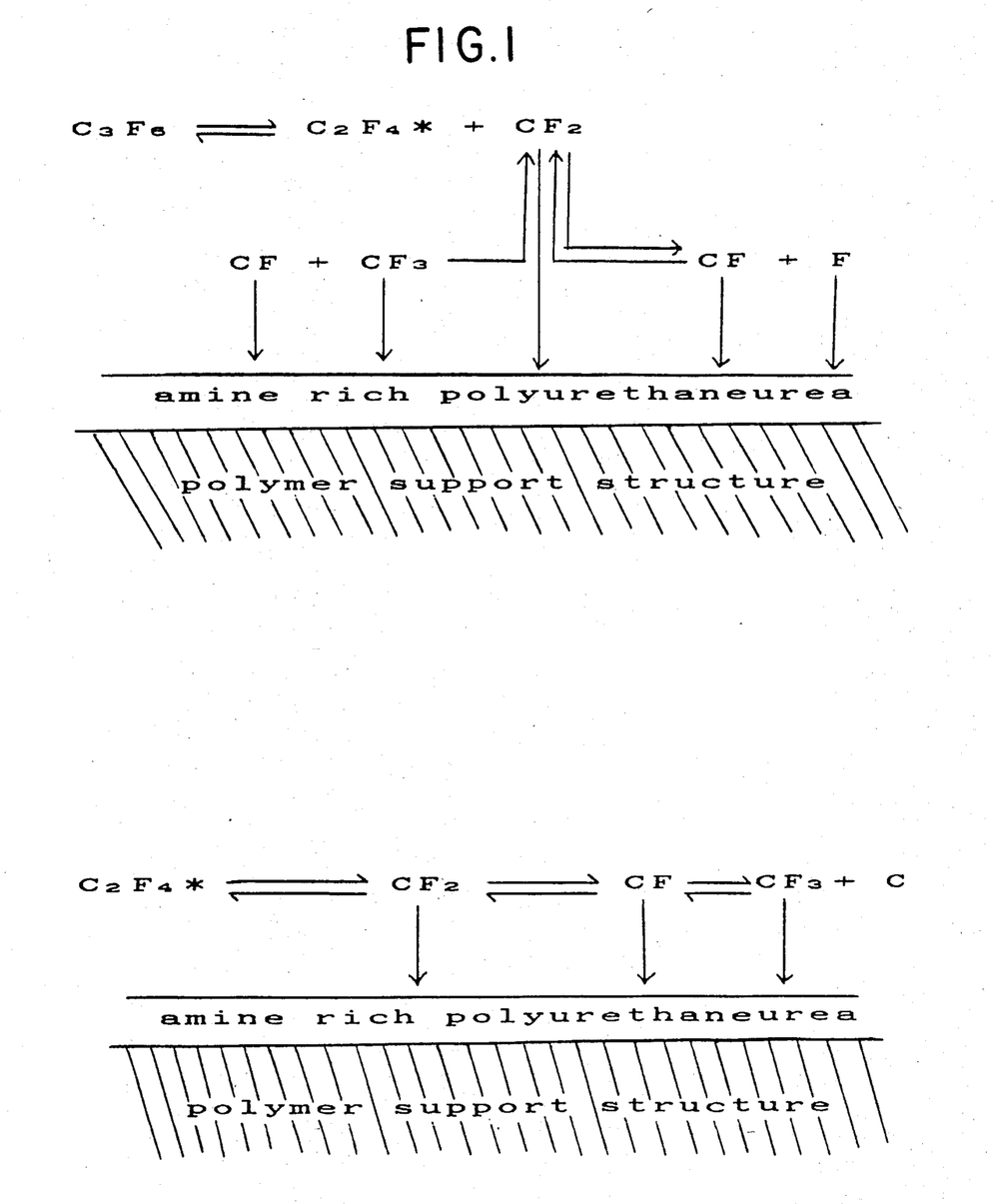
FIG. 1 shows a graphic illustration of the plasma treatment.

The plasma treatment covalently bonds radicals produced from the gas to the substrate surface. A graphic illustration is given in FIG. 1 using hexafluoropropylene as an example. As can be seen from the illustration, hexafluoropropylene dissociates into a number of different products.

The term antithrombogenic agent or material as used herein refers to any material which inhibits thrombus formation on its surface, such as by reducing platelet aggregation, dissolving fibrin, enhancing passivating protein deposition, or inhibiting one or more steps within the coagulation cascade and which forms an ionic complex with quaternary ammonium salts. Illustrative antithrombogenic materials may be selected from the group consisting of heparin, prostaglandins, sulfated polysaccharides, and mixtures thereof. Heparin is preferred. It should be understood that these materials are used in their natural form or as salts thereof, such as the sodium, or lithium salt. In addition to the foregoing antithrombogenic agents, optional supplemental amounts of antithrombogenic agents may also be used that are not reactive within the scope of the invention to further enhance the effects of the materials. Exemplary materials include urokinase, streptokinase, albumin and so forth.

The polymeric materials used in the invention as the solid support structure may be selected from a wide range of polymeric materials. The particular formulations do nor constitute a critical aspect of this invention other than to serve as a solid support structure for further treatment according to the inventive process.

Illustrative plastic materials useful as the support structure may be selected from the group consisting of polyethylene, polypropylene, polyurethanes, polyurethanesilicone copolymers, polyurethane-ureas, polycarbonates, silicone rubber, polyesters, nylons, natural rubber, polyvinyl chloride, acrylics, polystyrene, copolymers of polycarbonate and silicone rubber and mixtures thereof. The plastic materials are preferably preformed into the desired shape or structure for the particular application prior to treatment according to the invention.

The sequence of steps used to prepare the articles of this invention are essential to obtaining the desired antithrombogenic activity. The support structure should first be coated with the amine substrate. The coated support structure is then subjected to plasma treatment. Finally. the antithrombogenic agent is bonded to the amine substrate and the article is complete. If plasma treatment is performed as after the antithrombogenic agent is bonded to the amine substrate, it is likely that the ionization process may denature, inactivate or otherwise modify the antithrombogenic agent. Similarly, plasma treatment as a first step to coating with the amine substrate, would tend to increase adhesion of the coating to the support structure rather than increase the activity of the subsequently bonded antithrombogenic agent. Thus, it is essential to the inventive process and articles produced via this process that the steps be carried out in the sequence recited.

Figure 2:
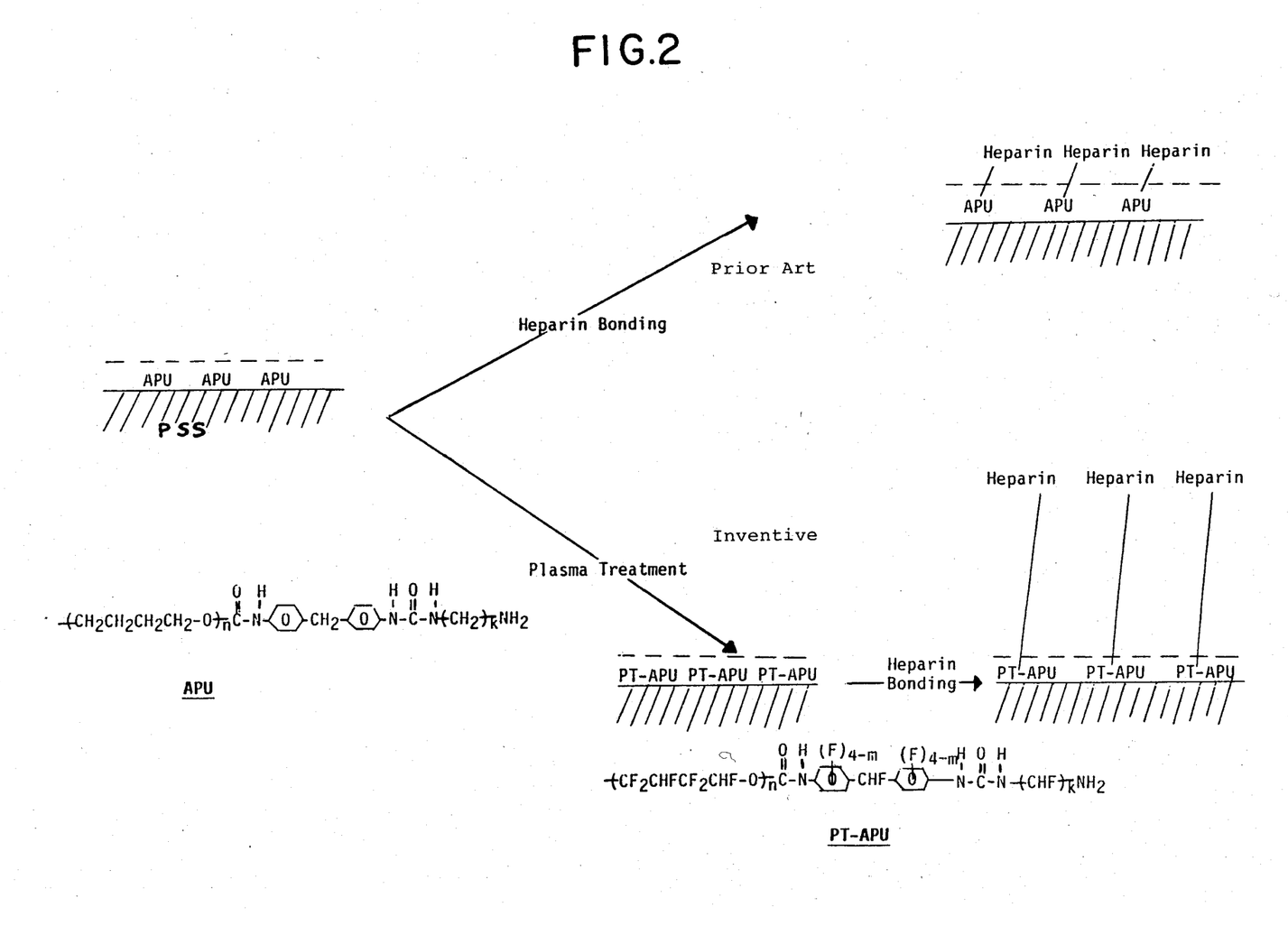
FIG. 2 is a graphic illustration of the process of producing the articles of the invention.

A preferred embodiment of the instant invention uses hexafluoropropylene as the gas for plasma treatment and uses a polyurethane solid support structure having an amine rich polyurethane urea coating bonded to heparin. FIG. 2 is a graphic illustration of the process of producing the articles of the invention, as well as depicting the prior art route of U.S. Pat. No. 4,521,564. The polymeric support structure (PSS) is shown as being coated with an amine rich polyurethane compound (APU). The prior art then bonded the antithrombogenic agent (heparin) to the APU. Heparin is shown as being closely held to the surface of the final product. The inventive process, however, is distinct in that prior to bonding of the heparin to the APU, the coated support structure is plasma treated to introduce hydrophobic character onto the substrate surface. FIG. 2 shows one of the probable chemical structures of the substrate surface subsequent to plasma treatment (PT-APU). The final product of the inventive process is intended to depict the physical extension of the heparin away from the surface of the substrate and the support structure due to repulsion by the hydrophobic character of the substrate surface, whereby the heparin is more available for contacting blood.

In the reaction equation scheme depicted, the polymeric solid support structure is contacted with an amine rich polyurethane urea substrate, which substrate provides a means for coupling with the antithrombogenic agent. The next step is plasma treatment with the desired gas (hexafluoropropylene) yielding hydrophobic groups on the surface of the substrate which "repel" the antithrombogenic group (heparin) next to be added. In the final step, aldehyde activated heparin is reacted with the substrate to form a structure wherein heparin is covalently coupled to the substrate. The resulting product demonstrates improved antithrombogenic efficacy as well as permanency and nonleachability.

Modification of the surface of the polymeric substrate using plasma treatment renders the substrate surface more hydrophobic. These hydrophobic groups minimize the interaction of the hydrophilic antithrombogenic group (e.g., heparin molecules) causing the latter to stay extended outwardly from the substrate surface, thereby making them more available for contacting blood and consequently more active in preventing thrombus formation.

As previously mentioned, one particularly preferred plastic solid support material is polyurethane polymers, which may contain conventional polyisocyanates, low molecular weight glycols and high molecular weight glycols. The polyisocyanates useful in the invention in introducing the urethane linkage into the polymer chain may be selected from a wide range of aliphatic, cycloalipathic and aromatic polyisocyanates. Useable diisocyanates may contain noninterferring groups, e.g., aliphatic hydrocarbon radicals such as lower alkyl or other groups, having substantially nonreactive hydrogens as determined by the Zerewitinoff test J. Am. Chem. Soc. 49,3181 (1927). The diisocyanate often has at least 6 carbon atoms and usually does not have more than about 40 carbon atoms. Diisocyanates of about 8 to 20 atoms in the hydrocarbon group are preferred. Suitable diisocyanates include 2,4-toluene diisocyanate; 2,6-toluene diisocyanate; 1,4-cyclohexane diisocyanate; dicyclohexylmethane 4,4'-diisocyanate: xylene diisocyanate: 1-isocyanate-3-isocyanatomethyl-3,5,5-trimethylcyclohexane: hexamethylene diisocyanate: methylcyclohexyl diisocyanate; 2,4,4-trimethylhexyl-methylene diisocyanate, isocyanates such as m-phenylene diisocyanate; mixtures of 2,4- and 2,6 hexamethylene-1,5-diisocyanate; hexahydrotolylene diisocyanate (and isomers). naphtylene-1,5-diisocyanate: 1-methoxyphenyl 2,4-diisocyanate diphenylmethane 4,4'-diisocyanate. 4,4'-biphenylene diisocyanate; 3,3 -dimethoxy-4,4biphenyl diisocyanate; 3,3-dimethyl 4,4'-biphenyl diisocyanate; and 3,3'dimethyl diphenylmethane 4,4'diisocyanate and mixtures thereof. The aliphatic and alicyclic diisocyanates employed in the process of this invention and the products made therefrom generally exhibit good resistance to the degradative effects of ultraviolet light.

The polyisocyanate compound used to form the prepolymers may contain a portion of polyisocyanates having two or more isocyanate (NCO) groups per molecule providing the urethane polymer compositions are not unduly deleteriously affected. The preferred polyisocyanate is selected from the group consisting of 4,4'-diphenylmethane diisocyanate, toluene diisocyanate, isophorone diisocyanate and methylene bis (4-cyclohexyl) diisocyanate.

The low molecular weight glycols and/or diamines may also be used to prepare the polymer which materials may have from 2 to 10 carbon atoms. Exemplary of these glycols are ethylene glycol, diethylene glycol, triethylene glycols, 1,4-butanediol, neopentyl glycol, 1,6-hexanediol, 1,8-octanediol, 1,2- and 1,3-propylene glycol, 2,3-butylene glycol. cyclo- hexane dimethanol (1,4-bis hydroxymethyl cyclohexane), dipropylene glycol, dibutylene glycol and 2-ethyl-2-(hydroxymethyl)-1,3- propanediol. Exemplary diamines include ethylenediamine, propanediamines, butanediamine, pentanediamine, hexanediamine, heptanediamine, octanediamine, 0-xylenediamine. 1,4-diaminocyclohexane, p-phenylenediamine, 1-methyl-2,4,diaminobenzene. bis(p-aminocylohexyl) methane, among others.

The high molecular weight glycols useful in the present invention may be a polyether diol or polyester diol and range in number average molecular weight from about 400 to about 3,000 and preferably about 500 to about 2,000. Examples ot suitable polyhydric alcohols are polypropylene glycols, polyethylene glycols and polybutylene glycols. polyesters of lactones, for example, ϵ-caprolactone or hydroxy carboxylic acids, for example, ω-hydroxycaproic acid, may also be used. Illustrative polyesters may contain hydroxyl groups, for example, reaction products of polyhydric alcohols reacted with divalent carboxylic acids. It is also possible to use the corresponding polycarboxylic acid anhydrides or corresponding polycarboxylic acid esters of lower alcohols or mixtures thereof, for producing the polyesters. The polycarboxylic acids may be aliphatic, cycloaliphatic, aromatic and/or heterocyclic and may optionally be substituted, for example, by halogen atoms and/or unsaturated. Examples of polycarboxylic acids of this kind include succinic acid, adipic acid, suberic acid, azelaic acid, sebacic acid, phthalic acid, phthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalic acid dimethyl ester and terephthalic acid dimethyl ester and terephthalic acid bis-glycol ester.

The polyethers containing at least 2, generally 2 to 8, but preferably 2 to 3 hydroxyl groups used in accordance with the invention are also known per se and are obtained, for example, by polymerizing epoxides. such as ethylene oxide, propylene oxide, tetrahydrofuran, styrene oxide or epichlorohydrin on their own. for example, in the presence of $BF_3$, or by adding these epoxides, optionally in admixture or in succession, to starter. components containing reactive hydrogen atoms, such as water, alcohols, or amines, for example, ethylene glycol. 1,3- or 1,2-propylene glycol, 4,4'-dihydroxy diphenyl propane, aniline, ammonia, ethanolamine or ethylene diamine. The most preferred polyether diols are polybutylene glycols.

While the preferred polyurethane and/or polyurethane urea compositions of the invention are small amounts of crosslinking agents to the compositions when they are coated onto the support in order to render them thermosetting. Suitable crosslinking agents are discussed above and include the listed diisocyanate compounds.

It should be recognized that the products of this invention are useable in a wide variety of devices designed for contacting body fluids. Exemplary articles which can be in contact with body fluids such as blood, include artificial organs, vascular grafts, probes, cannulas, catheters, hemodialysis tubing, hyperalimentation catheters and other long indwelling vascular catheters, and the like. A particularly preferred application, of the products of the invention is in catheter type devices wherein the inventive compositions are coared on either or both interior and exterior surfaces of the catheter.

The invention will be further illustrated by the following non-limiting examples. All parts and percentages given throughout the specification are by weight unless otherwise indicated.

EXAMPLE 1

This example demonstrates the preparation of the amine compound. This compound is used to coat the support structure of the instant invention prior to plasma treatment. Trimethylolpropane (44.73 grams)

and 337.59 grams of a low molecular weight polyether polyol (Terathane 650) were added together in a mixing vessel (1 equivalent of each) and heated to about 45° C. The materials were then mixed thoroughly and 524.00 grams (4 equivalents) of hydrogenated diphenylmethylene diisocyanate were added. Dibutyl tin dilaurate in the amount of 14 grams (0.015%) was added to the mixing solution. After 5 minutes of mixing, the reactants were transferred to a 90° C. oven for 60 minutes. The prepolymer was then purged with nitrogen and stored.

Fifteen grams of this prepolymer were added to 30 grams of toluene to make a 33% wt/wt solution. A separate diamine solution was prepared by adding 4.1 grams of 1,6-hexanediamine to 20 grams of isopropanol and 10 grams of toluene. The diamine solution was stirred vigorously with a magnetic stir bar under nitrogen. The prepolymer solution was then added dropwise to the diamine solution over a two hour period. The reaction was stirred for an additional two hours. Glacial acetic acid (2.3 grams) was then added dropwise to the reaction mixture. The resulting composition was an amine rich polyurethaneurea polymer, which was then dried with nitrogen gas and finally with a vacuum.

The amine rich polyurethane urea composition was then dissolved in methanol to a 20% wt/wt solution for deposition on the polymeric support structure.

EXAMPLE 2

This example demonstrates a method of preparing an aldehyde activated heparin which is to be covalently bonded to the amine substrate prepared in Example 1. (A) shows radioactive labelled heparin. (B) shows non-labelled heparin.

(A) preparation of Aldehyde Activated Radioactive Labelled Heoarin

Seventy-five (75) mls of water were added to a beaker which contained 150 mls of 1% $^3$H-heparin solution. Then 1.5 grams of sodium acetate was transferred to the beaker. The pH of this solution was adjusted to 4.5 with glacial acetic acid. Sodium periodate (NaIO$_4$) in the amount of 0.075 grams of was added and the solution was reacted for 20 minutes in a light protected reaction vessel with constant stirring. At the end of the reaction, 2.26 grams of glycerin was added to neutralize any remaining periodate. The solution was dried down overnight under nitrogen. Then the solution was reconstituted to 2% and the pH of the solution was adjusted to 6.6 by the dropwise addition of 10N NaOH. The aldehyde activated $^3$H-heparin solution was ready for bonding to the amine compound. It should be noted that other types of radioactive labelled heparin other than $^3$H are useful.

(B) preparation of Aldehyde Activated Heparin 7.5 grams of heparin was dissolved in 1125 mls of distilled water. Three (3.0) grams of sodium acetate was weighted and transferred to the heparin solution. The pH of this solution was then adjusted to 4.5 with glacial acetic acid. Sodium periodate (NaIO$_4$) was added in the amount of 0.375 grams and the solution was reacted for 20 minutes in a light protected reaction vessel with constant stirring. At the end of the reaction, 11.30 grams of glycerin was added to neutralize any remaining periodate. Then the solution was reconstituted to 2%. The pH of the solution was adjusted to 6.6 by the dropwise addition of 10N NaOH. The aldehyde activated heparin solution was ready for bonding to the amine compound.

EXAMPLE 3

This example illustrates the preparation of an article having increased antithrombogenic activity utilizing the concepts of the present invention. The amine rich polyurethane urea (APU) substrate of Example was dissolved in methanol to a 20% wt/wt solution. A polyurethane support structure was coated with the APU. After coating, the substrate was placed in the nitrogen atmosphere at ambient temperature for 60 minutes. The coated tubing was then treated with hexafluoropropylene plasma (0.3 torr and 50 watts) for 15 minutes. using the plasma treatment unit manufactured by Branson-/IpC (Model p-2075).

The samples were then placed in a reaction vessel which contained 0.025 g (2.5% weight heparin) sodium cyanoborohydride and 2% aldehyde activated $^3$M-heparin, prepared via Example 2. The reaction was performed in a pH 6.6 aqueous solution at 50° C. Two hours later, the samples were removed and placed in a 3M saline solution for one hour to remove any loosely bonded or adsorbed heparin. Then these samples were re-reacted for a second two hour period at the same conditions as described above. Initial radiolabel assays showed that 87.8±12.9 micrograms of heparin was bonded per cm$^2$ of surface area as compared to the control samples (143.4±3.3 micrograms per cm$^2$) which were identically treated in all respects except without plasma treatment. After a dynamic leach scudy in 3M saline solution for 24 hours, the radiolabelled assay still showed 79.4±6.3 micrograms of heparin bonded per cm$^2$ of surface area. In comparison, the controls showed 103.7±13.1 micrograms of heparin bonded per cm$^2$ of surface area. This demonstrates the permanency of the covalently bonded heparin of this invention.

EXAMPLE 4

This example demonstrates the increased antithrombogenic activlty of the present invention compared to control samples prepared identically in all respects except without plasma treatment.

Two sets of polyurethane tubings were coated with the amine rich polyurethaneurea compound having heparin bonded thereon as described in Example 3. One set of samples was exposed to hexafluoropropylene plasma treatment and the other set of samples used as the control did not receive the plasma treatment.

Those samples to be plasma treated were then placed in a reaction vessel which contained 0.25 g (2.5% of heparin weight) sodium cyanoborohydride and 2% aldehyde activated heparin. The plasma reaction was conducted as described in Example 3.

An in vivo study was performed in such a way that one plasma treated sample was inserted into one external jugular vein of a dog, while the control sample was inserted in the other jugular vein of the same animal. The activity of bonded heparin was demonstrated by the loss of platelet adhesion (platelet uptake slope) and low thrombus weight. The average slope and thrombus weight of three dogs are listed as follows:

|  | Plasma Treated Samples | Control Samples |
| --- | --- | --- |
| Slope | 0.0188 ± 0.0025 | 0.0413 + 0.0266 |

| -continued | |
|---|---|
| Plasma Treated Samples | Control Samples |
| Thrombus weight 4.53 mg ± 1.89 mg | 14.13 mg ± 3.09 mg |

Figure 3:
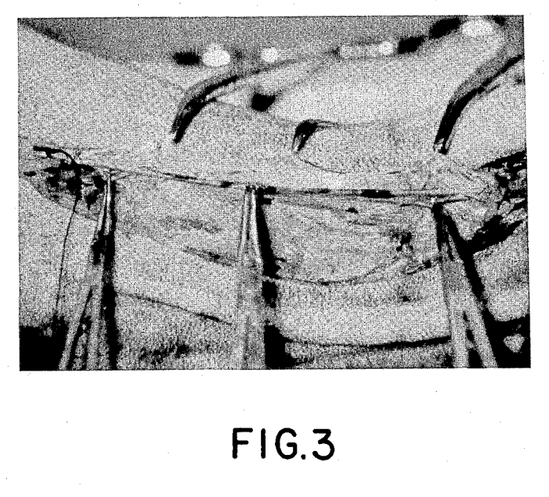
FIG. 3 shows a picture of the tubing treated with the control sample.
Figure 4:
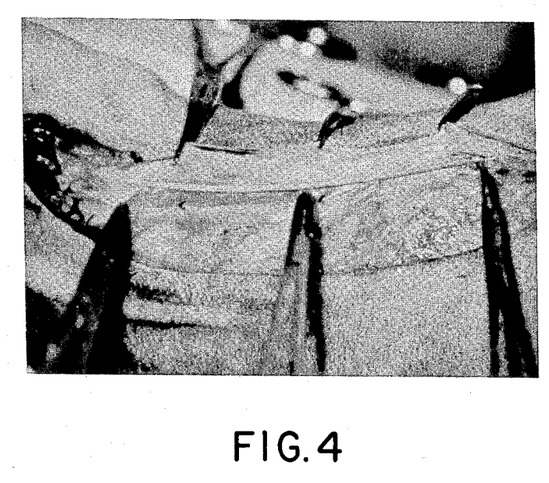
FIG. 4 shows the tubing treated with composition of the invention.

It is clear that the activity of the bonded heparin was enhanced through plasma treatment as indicated by the lower slope value and the lower thrombus weight. The photographs in FIGS. 3 and 4 clearly show the enhanced antithrombogenic activity of the instant invention. FIG. 3 shows a picture of the tubing treated with rhe control sample and FIG. 4 shows the tubing treated with the inventive composition. Both pictures were taken after leaving the tubes in the animal for 40 minutes.

EXAMPLE 5

This example demonstrates the use of a polyethyleneimine compound as the amine substrate. Thermoplastic polyurethane tubing (support structure) was placed in a borate buffer solution (pH 9) containing 0.5% glutaraldehyde and 0.1% polyethyleneimine (PEI) at room temperature for 30 minutes to allow deposition and bonding of the amine compound to the tubing. After rinsing with water the tubing was incubated in an aqueous solution of dextran sulfate (1 mg/ml, 0.15M Nacl, 50° C., pH 3) for 5 minutes and was then rinsed with water. Then the tubing was incubated in a 1% PEI solution at pH 9 for 5 minutes and was carefully rinsed with water. After drying the tubing in the nitrogen atmosphere at ambient temperature for 60 minutes. the tubing was treated with hexafluoropropylene plasma (0.3 torr and 50 watts) for 15 minutes, using the plasma treatment unit manufactured by Branson/IpC (Model p-2075).

The sample was then placed in a reaction vessel which contained 0.25 g (2.5% of heparin weight) sodium cyanoborohydride and 2% aldehyde activated heparin. The reaction was conducted as described in Example 3, producing a product with excellent antithrombogenic properties.

The invention being thus described, it will be obvious that the same may be varied in many ways. Such variations are not to be regarded as a departure from the spirit or scope of the invention and all such modifications are intended to be included within the scope of the claims.

We claim:

1. An article having antithrombogenic properties comprising:
   (a) a polymeric support structure;
   (b) a polymeric material rich in amine content which serves as a substrate for an antithrombogenic agent, said matrial being selected from the group consisting of primary amines having a carbon chain length of from 2 to 10,000, a polyalkylenimine having 2 to 4 carbon atoms per amine unit and mixtures thereof, said material being bonded to the support structure;
   (c) a hydrophobic group covalently bonded to said material; and
   (d) an antithrombogenic agent covalently bonded to said material, wherein the activity of the antithrombogenic agent is enhanced by said hydrophobic group.

2. The article of claim 1 wherein the support structure is selected from the group consisting of a polyurethane, polyethylene, polypropylene, polyurethane-silicone, polyurethaneurea, polycarbonate, silicone rubber, polyester, nylon, natural rubber, polyvinyl chloride, acrylic, polystyrene, copolymer of polycarbonate and silicone rubber and mixtures thereof.

3. The article of claim 1 wherein the antithrombogenic material is selected from the group consisting of heparin, prostaglandins, urokinase, streptokinase, sulfated polysaccharide, albumin and mixtures thereof.

4. The article of claim 1 wherein the polyalkylenimine is selected from the group consisting of polyethylenimine, polypropylenimine, polybutylenimine and mixtures thereof.

5. The article of claim 1 wherein the polymeric support structure is a polyurethane medical device for use in contact with blood.

6. The article of claim 1 wherein the material is selected from the group consisting of a polyurethaneurea, polyamide, polyimide, polyvinylamine, polyalkylenimine and mixtures thereof.

7. The article of claim 6 wherein the polyurethaneurea is selected from the group coonsisting of a polyether based urethaneurea, a polyester based urethaneurea, a polybutadiene urethaneurea and mixtures thereof.

8. The article of claim 7 wherein the polyurethaneurea is selected from the group consisting of poly(ethylene oxide) urethaneurea, poly(propylene oxide) urethaneurea, poly(tetramethylene oxide) urethaneurea; poly(ethylene adipate) urethaneurea, poly(propylene adipate) urethaneurea, poly(tetramethylene adipate) urethaneurea, poly(hexamethylene adipate) urethaneurea; polycaprolactone urethaneurea; and mixtures thereof.

9. The article of claim 1 wherein the hydrophobic group is selected from the group consisting of fluorine compounds; siloxane compounds selected from the group having the formulas wherein $R_1$, $R_2$ and $R_3$ are aliphatic or substituted aliphatic groups having an aliphatic carbon chain length of from 1 to 4 carbons and n is an integer from 1 to 100; silazane compounds selected from the group having the formula wherein $R_1$, $R_2$, $R_3$ and $R_4$ are alkyl groups having 1 to 4 carbons and hydrogen; silane compounds selected from the group having the formula wherein $R_1$, $R_2$, $R_3$ and $R_4$ are aliphatic groups, substituted aliphatic groups, aromatic groups, substiaromatic groups, halogens, alkoxyl groups, vinyl groups and mixtures thereof.

10. The article of claim 9 wherein the fluorine compound is selected from the group consisting of dichlorodifluoromethane, chlorotrifluoromethane, bromotrifluoromethane, tetrafluoromethane, chlorodifluoromethane, fluoroform, 1,2-dichlorotetrafluoroethane, hedafluoroethane, tetrafluoroethane, hexafluoropropylene, boron trifluoride, silicon tetrafluoride, sulfur hexafluoride, sulfur tetrafluoride, tungsten hexafluoride, fluorine and mixtures thereof.

11. An article having enhanced antithrombogenic activity produced by the process of:
(a) bonding to a polymeric support structure an amine-rich material selected from the group consisting of a primary amine having a carbon chain length of 2 to 10,000, a polyalkylenimine having 2 to 4 carbon atoms per amine unit and mixtures thereof;
(b) plasma treating the amine-rich material in the presence of a gas to bond a hydrophobic group thereto; and
(c) covalently bonding an antithrombogenic agent to said amine-rich material.

12. The article of claim 11 wherein the polymeric support structure is a polyurethane.

13. The article of claim 11 wherein said gas is hexafluoropropylene.

* * * * *